United States Patent [19]
Awakowicz et al.

[11] Patent Number: 6,162,405
[45] Date of Patent: Dec. 19, 2000

[54] ARRANGEMENT FOR STERILIZING A CONTAINER WITH LOW-PRESSURE PLASMA

[75] Inventors: Peter Awakowicz, Munich; Robert Frost, Landshut, both of Germany

[73] Assignee: Ruediger Haaga GmbH, Altobergdorf, Germany

[21] Appl. No.: 09/240,680

[22] Filed: Feb. 2, 1999

[30] Foreign Application Priority Data

Feb. 24, 1998 [DE] Germany ............... 198 07 742

[51] Int. Cl.[7] .................................. B01J 19/08
[52] U.S. Cl. .................. 422/186.06; 422/186.05; 422/907
[58] Field of Search ............... 422/186.06, 186.05, 422/907

[56] References Cited

U.S. PATENT DOCUMENTS

| | | | |
|---|---|---|---|
| 3,701,628 | 10/1972 | Ashman et al. | 21/54 R |
| 4,056,007 | 11/1977 | Luckan | 204/177 |
| 4,221,972 | 9/1980 | Oppel et al. | 422/186.06 |
| 5,194,291 | 3/1993 | D'Aoust et al. | 422/186.06 |
| 5,243,259 | 9/1993 | Sato et al. | 204/298.37 |

*Primary Examiner*—Kishor Mayekar
*Attorney, Agent, or Firm*—Evenson, McKeown, Edwards & Lenahan, P.L.L.C.

[57] ABSTRACT

An arrangement sterilizes metal cans with a low-pressure plasma. The necessary reactor is formed by two electrodes Inserted into one another, whereby an annular gap remains for the container sleeve. The metal can is connected electroconductively with the outer electrode. The sterilizing plasma can hereby be ignited between the inner electrode and the inner surfaces of the metal can.

16 Claims, 2 Drawing Sheets

ARRANGEMENT FOR STERILIZING A CONTAINER WITH LOW-PRESSURE PLASMA

BACKGROUND OF THE INVENTION

This application claims the priority of German application No. 198 07 742.4, filed Feb. 24, 1998, the disclosure of which is expressly incorporated by reference herein.

The present invention relates to an arrangement for sterilizing the inner surfaces of a container comprising a filling opening and a wall having at least one electroconductive layer, also comprising a reactor, which takes up the container. The reactor generates a low pressure plasma. A vacuum pump is connected to the reactor, and a conduit leads into the reactor for supplying the gas to be ionized. A first electrode can be inserted in through the filling opening into the container, and a second electrode is located outside of the container, with a high frequency generator connected to one of the electrodes.

FIG. 3 in U.S. Pat. No. 3,701,628 shows how to sterilize a container located in a reactor by way of a low-pressure plasma. The electroconductive metal walls of the reactor serve as a grounded electrode. The other electrode, connected to the high frequency generator, can be inserted through the container opening into the inside of the container. The dielectric sleeve of the container, for example of a milk carton, can comprise a layered material, of which one layer is electroconductive. The container itself stands on an insulated platform.

The sterilizing effect of the plasma to be ignited is based on a mechanical destruction of the microorganisms by ion bombardment as well as on a chemical destruction. In order to accelerate the ions to a high bombardment level, the highest possible potential difference between the plasma and the container is necessary. As, in the known arrangement, the container is located insulated between the electrodes, the wall to be sterilized is charged to the more negative, in relation to the plasma, so-called floating potential. The arising potential difference of several volts is very low and of barely any influence, the degree of effectiveness thus not being very good.

SUMMARY OF THE INVENTION

An object of the present invention is to alter the above mentioned arrangement such that such containers can be sterilized with considerably improved effectiveness, whereby the wall is totally, or to a great extent, electroconductive.

This object has been achieved according to the present invention in that the electroconductive layer of the container wall is connected electroconductively to the second electrode.

In such an embodiment, the electroconductive layer, or in particular cases the entire wall itself, becomes the second electrode. Thus the inner wall of the container is hit in periodically recurring timespans by a potential negative in relation to the plasma. This potential exceeds the above-mentioned floating potential by a count of one or two times the power of ten. This strongly increased potential difference can then be utilized for a strong ion bombardment when the wall which is to be sterilized becomes the second electrode. As long as the second electrode is grounded, this strongly increased potential difference occurs during the positive half wave of the high frequency voltage.

Although the metal container is arranged inside of a reactor, the metal container itself becomes a reactor as a result of the above mentioned measures, whereby the sleeve is surrounded on the inside and outside by a vacuum. Impairments to the form stability of the container are hereby avoided.

Often the metal sleeve of containers, for example metal cans, is covered by a non-electroconductive layer on the outside, which is printed with advertising. In such a case, however, the electroconductive sleeve is connected electroconductively to the bottom of the container. In an embodiment of the present invention, therefore, the electroconductive layer of the sleeve is connected to the second electrode by the electroconductive bottom of the container. This can be done in such a way that, for example, the second electrode has a corresponding bottom, on which the container is placed. Alternatively, the sleeve can, of course, be contacted by the second electrode below the printed layer. In an aluminum container, which is in general covered by a non-electroconductive oxide layer, contact must be achieved through the non-electroconductive layer.

In a further embodiment of the present invention, the second electrode can surround the sleeve of the container from the outside at least in the area of its filling opening. Thereby, the plasma in the area of the filling opening can extend also to the outer surface and perform sterilization there. The first electrode and the second electrode can form, if required, a large annular gap between them, in which the sleeve of the container is located. The plasma is hereby ignited between the inner surfaces of the container and the first electrode, so that primarily the inner surfaces of the container are sterilized. In such an embodiment, the reactor can essentially be formed by the two electrodes exclusively.

In a particularly advantageous embodiment of the present invention, a constant voltage supply can be connected to the electrode which is connected with the high frequency generator. With this constant voltage supply, the potential ratios can be influenced such that the potential difference between the plasma and the wall of the container to be sterilized is increased by the amount of the constant current. According to whichever of the two electrodes is connected to the high frequency generator, the direct voltage must be positive or negative. This results, on a temporal or time average, in a significantly increased ion bombardment, which in turn results in shorter treatment times. The determination efficiency of the plasma can thus be actively regulated.

BRIEF DESCRIPTION OF THE DRAWINGS

These and further objects, features and advantages o the present invention will become more readily apparent from the following detailed description thereof when taken in conjunction with the accompanying drawings wherein.

DETAILED DESCRIPTION OF THE DRAWINGS

Figure 1:
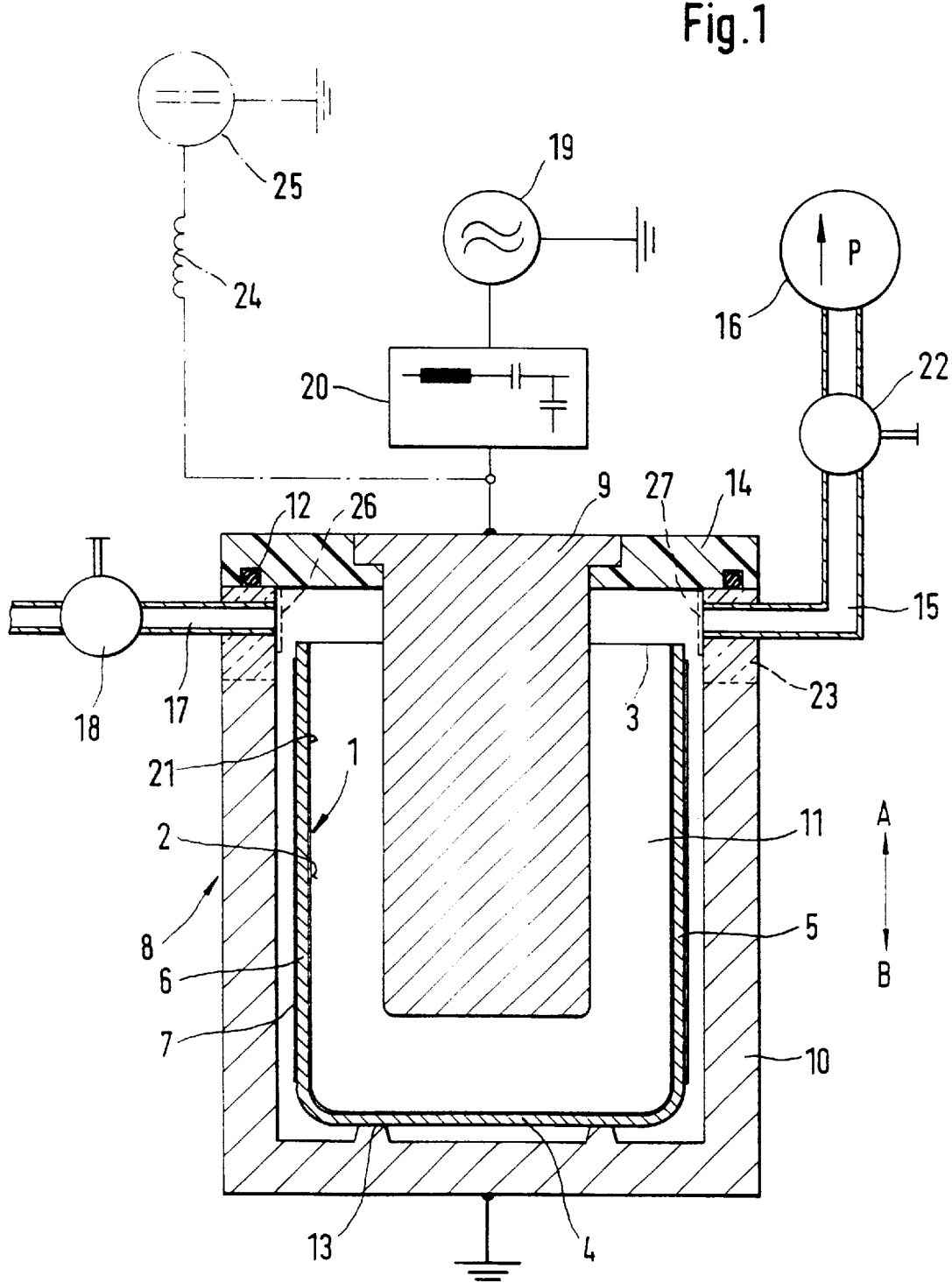
FIG. 1 is a schematic cross-sectional elevations view of an arrangement according to the present invention, in which the first electrode is connected to a high frequency generator.

The arrangement shown in FIG. 1 serves the sterilization of containers 1 by way of a low-pressure plasma. The containers 1 comprise inner surfaces 2, which are, as a rule, provided with an enamel coating 21. The containers also comprise a filling opening 3 as well as an electroconductive bottom 4. The sleeve 5, aside from the enamel coating 21, can be either entirely or to a great extent also electroconductive, for example the sleeve 5 may comprise an electroconductive supporting layer 6 as well as an outer non-electroconductive layer 7 which can be printed for advertising purposes. The electroconductive layer 6 of the sleeve 5 is connected electroconductively with the bottom 4. The containers 1 may be metal cans, for example, as are used for beer or other beverages.

The container 1 to be sterilized is taken up in the inside of a reactor 8, which is in the present case formed essentially by a first (inner) electrode 9 and a second (outer) electrode 10. The first electrode 9, which can be inserted through the filling opening 3 into the container 1, is connected to an alternating voltage as described below. The second electrode 10, which itself can have a container-like form, is grounded and surrounds the sleeve and the bottom 4 of the container 1 completely, thus forming a wall of the reactor 8.

During operation, the two electrodes 9, 10 can be inserted telescope-like into one another with the aid of an intermediary ring seal 12. They can be moved apart in the directions according to double-headed arrows A, B for the insertion of a container 1 and subsequently sealed closed again. The vacuum thus prevails on both sides of the sleeve 5, although the sterilizing plasma forms essentially only between the sleeve 5 and the first electrode 9. Thereby, the inner surfaces 2 of the container 1 as well as its outer surfaces in the area of the filling opening 3 are sterilize.

The Bottom 4 of the container-like second electrode 10 comprises a supporting surface 13, on which the bottom 4 of the container 1 is electroconductively supported. In this way, the electroconductive layer 6 of the sleeve 5 becomes an extension of the second electrode 10, the layer 6 itself thus forming an electrode. Although the reactor 8 is formed by the electrodes 9, 10, she actual reactor, in relation To the ignited plasma, is the annulus 11 between the inner surfaces 2 of the container 1 and the outer surfaces of the first electrode 9.

The reactor 8 is sealed closed by an electrically insulated closing component 14. A suction pipe 15 enters the reactor 8 and is connected with the aid of a valve 22 to a vacuum pump 16. The vacuum pump 16 is configured for operational pressures between 1 and 100 Pa. Low pressures of the plasma to be ignited result at the same time in low treatment temperatures.

A supply pipe 17 for ionized gas enters the reactor 8. The flow of the gas is regulated by a choker valve 18. Gases such as, for example, hydrogen or helium can be used, as these gases have the lightest and smallest possible ions, while having at the same time a high ionization energy. Hydrogen peroxide can also be considered because it increases the sterilization effect by the formation of microbicide functioning radicals.

The openings of the suction pipe 15 and the supply pipe 17 located in the reactor 8 are preferably each covered with an electroconductive net 26 or 27, whose mesh size is so small that it is previous for gas but impervious to plasma. This prevents the plasma from burning at the suction pipe 15 and the supply pipe 17 connections, while also preventing the plasma from being suctioned off by a possible pumping action.

The first electrode 9 is connected to a high frequency generator 19, which is configured for 13.56 MHz. The alternating voltage is transmitted to the plasma to be formed by an adapter network 20.

In the container 1 which is essentially made of metal, the sterilization of the inner surface 2 of the sleeve 5 and the inner surface of the bottom 4 is primarily involved. In the area of the filling opening 3, a small part of the outer surface of the container 1 should, however, also be sterilized and is made possible by the shown arrangement of the electrodes 9, 10. The electrodes 9, 10 project somewhat out over the upper edge of the container 1 so that a plasma is ignited also in this area 23, i.e. at the upper edge of the sleeve 5.

The effect of the arrangement is based on the fact that the electroconductive layer 6 of the sleeve 5 is connected electroconductively to the second electrode 10 and thus becomes itself an electrode. The electroconductive layer 6 does not form a power block between the electrodes 9, 10 but rather forms an electrode itself which operates in conjunction with the first electrode 9. This results further in the plasma being ignited essentially only in the annulus 11 between the sleeve 5 and the first electrode 9, whereby the container 1 forms the actual reactor space. Because, however, the sleeve 5 is surrounded on the inside and outside by low pressure, the form stability of the container 1 is in no way impaired.

As shown by dot-dash lines, the first electrode 9, which is connected to the high frequency generator 19, can in addition be connected to a direct current source 25 having a positive direct voltage. A coil 24 is arranged hereto. The regulatable amount of direct voltage increases the potential difference between the plasma and the inner surfaces 2 of the container 1.

Figure 2:
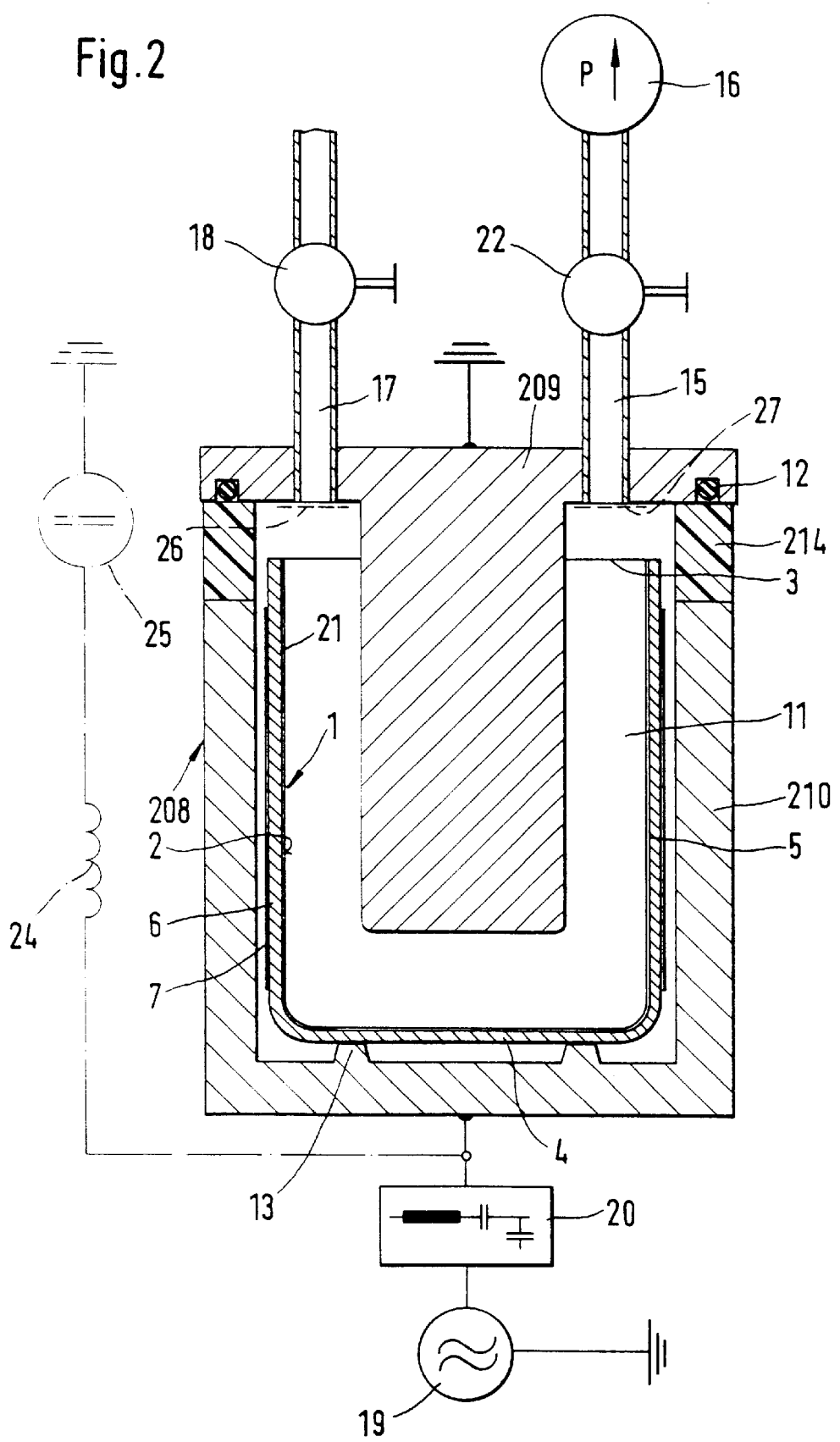
FIG. 2 is a view similar to FIG. 1 but of a second arrangement according to the present invention, in which the second electrode is connected to a high frequency generator.

The embodiment of the present invention as shown in FIG. 2 differs from the embodiment shown in FIG. 1 essentially in that the high frequency generator 19 is connected by an adapter network 20 not to the first electrode 209, but rather to the second electrode 210. Again, a direct current source 2, dented only by a dot-dash line, can be additionally connected to the electrode 210 by a coil 24, with the direct voltage having to be negative.

Again, as shown in FIG. 2, the reactor 208 is essentially formed only by two electrodes 209, 210. In the area of the filling opening 3 of the container 1, the outer electrode 210 is provided with an insulator 214 which insulates the electrode 210 against the electrode 209.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An arrangement for sterilizing inner surfaces of a container having a filling opening and a wall with at least one electroconductive layer, comprising a reactor for receiving the container, a vacuum pump operatively connected to the reactor, a conduit inserted into the reactor for supplying an ionization gas, a first electrode which is insertable through the filling opening into the container, a second electrode located externally of the container, and a high frequency generator operatively connected to one of the electrodes and configured to excite the electrode to generate a law pressure plasma and to sterilize the inner surfaces of the container, wherein said electroconductive layer is connected electroconductively with the second electrode.

2. An arrangement according to claim 1, wherein the electroconductive layer is connected with the second electrode via an electroconductive bottom of the container.

3. An arrangement according to claim 1, wherein the second electrode surrounds a sleeve of the container outside thereof at least in a region of the filling opening.

4. An arrangement according to claim 3, wherein the electroconductive layer is connected with the second electrode via an electroconductive bottom of the container.

5. An arrangement according to claim 1, wherein the reactor is formed essentially by said two electrodes.

6. An arrangement according to claim 5, wherein the electroconductive Layer is connected with the second electrode via an electroconductive bottom of the container.

7. An arrangement according to claim 6, wherein the second electrode surrounds a sleeve of the container outside thereof at least in a region of the filling opening.

8. An arrangement according to claim 1, wherein a direct current source is connected to the electrode which is connected to the high frequency generator.

9. An arrangement according to claim 8, wherein the electroconductive Layer is connected with the second electrode via an electroconductive bottom of the container.

10. An arrangement according to claim 9, wherein the second electrode surrounds a sleeve of the container outside thereof at least in a region of the filling opening.

11. An arrangement according to claim 10, wherein the reactor is formed essentially by said two electrodes.

12. An arrangement according to claim 1, wherein at least one of the opening of a suction pipe connected to the vacuum pump, and an opening of a supply pipe, located in the reactor are covered with a plasma-impervious electroconductive net.

13. An arrangement according to claim 12, wherein the electroconductive layer is connected with the second electrode via an electroconductive bottom of the container.

14. An arrangement according to claim 13, wherein the second electrode surrounds a sleeve of the container outside thereof at least in a region of the filling opening.

15. An arrangement according to claim 14, wherein the reactor is formed essentially by said two electrodes.

16. An arrangement according to claim 15, wherein a direct current source is connected to the electrode which is connected to the high frequency generator.

* * * * *